Figure 1:
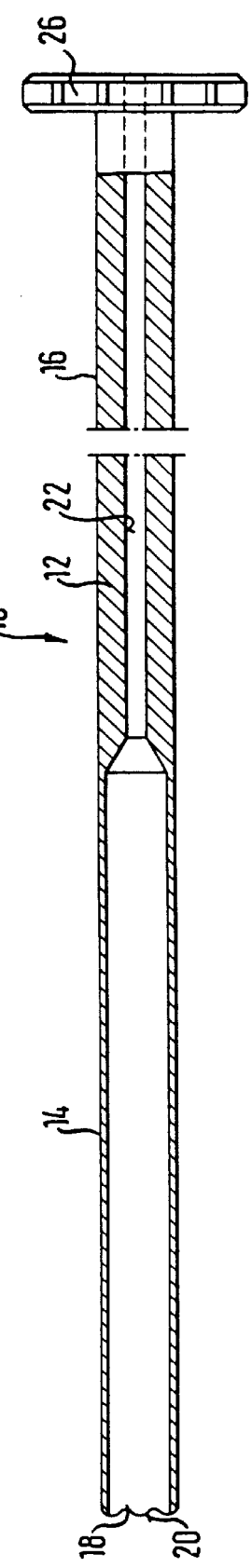

United States Patent [19]

Semm

[11] Patent Number: 5,879,358
[45] Date of Patent: Mar. 9, 1999

[54] CERVICAL PUNCH

[75] Inventor: Kurt Semm, Kiel, Germany

[73] Assignee: WISAP Gesellschaft fuer wissenschaftlichen Apparatebau mbH, Sauerlach, Germany

[21] Appl. No.: 64,142

[22] PCT Filed: Jan. 24, 1992

[86] PCT No.: PCT/EP92/00150

§ 371 Date: Dec. 21, 1994

§ 102(e) Date: Dec. 21, 1994

[87] PCT Pub. No.: WO92/12676

PCT Pub. Date: Aug. 6, 1992

[30] Foreign Application Priority Data

Jan. 25, 1991 [DE] Germany ............... 9100873 U
Oct. 2, 1991 [DE] Germany ............... 9112303 U
Nov. 19, 1991 [DE] Germany ............... 9114443 U

[51] Int. Cl.⁶ ............................ A61B 17/42; A61B 17/14
[52] U.S. Cl. ........................ 606/119; 606/184; 606/180
[58] Field of Search ................... 606/1, 79, 80, 606/119, 167, 170, 180, 184, 185, 127; 128/749, 751–755

[56] References Cited

U.S. PATENT DOCUMENTS

| | | | |
|---|---|---|---|
| 4,142,517 | 3/1979 | Stavropoulos | 606/79 |
| 4,306,570 | 12/1981 | Matthews | 606/179 |
| 4,461,305 | 7/1984 | Cibley | 606/180 |
| 4,543,966 | 10/1985 | Islam et al. | 128/754 |
| 4,573,448 | 3/1986 | Kambin | 606/179 |
| 4,696,308 | 9/1987 | Meller et al. | 606/180 |
| 4,785,826 | 11/1988 | Ward | 128/754 |
| 4,798,213 | 1/1989 | Doppelt | 128/754 |
| 4,913,143 | 4/1990 | Oloff | 606/179 |
| 5,040,542 | 8/1991 | Gray | 606/179 |
| 5,049,150 | 9/1991 | Cozad | 606/96 |
| 5,271,414 | 12/1993 | Partika et al. | 128/754 |
| 5,341,816 | 8/1994 | Allen | 128/754 |
| 5,372,583 | 12/1994 | Roberts et al. | 128/754 |

FOREIGN PATENT DOCUMENTS

WO88/10098  12/1988  WIPO.

*Primary Examiner*—Glenn K. Dawson
*Attorney, Agent, or Firm*—Evenson, McKeown, Edwards & Lenahan, P.L.L.C.

[57] ABSTRACT

A cervical punch has a hollow cylindrical circular morcellator tube, which is provided with a cutting region having an all-round wave grinding pattern around the distal opening. The morcellator tube, which can also be referred to as the basic body, receives a guide rod along which is possible an axial and/or rotary movement of the morcellator tube in a direct or indirect manner by a guide cylinder.

5 Claims, 4 Drawing Sheets

CERVICAL PUNCH

The invention relates to a cervical punch or biopsy clamp for the decortication of the cervical fasciae from the uterine tissue for uterine extirpation.

It has hitherto been conventional practice to completely remove the uterus when there is a benign change indication. However, in the attempt to endoscopically remove the uterus, difficulties are encountered in the decortication of the cervix from the highly vascular pericervical tissue.

The object of the invention is to provide a medical instrument able to very carefully remove the uterine tissue in a clearly defined area of the cervix.

According to the invention this object is achieved by the cervical punch according to claim 1. Advantageous further developments of the invention form the subject matter of subclaims.

The risk of a malignant degeneration of the genital canal left behind after supracervical uterus removal emanates almost exclusively from the transition area in the vicinity of the portio cervicalis, the endothelium of the cervix and the endometrium. Whereas hitherto the cervical fasciae have been removed from the surrounding tissue from the outside, i.e. the uterine artery, the uterine veins, the urethra, the periureteral tissue and the corresponding neuroplexus, the present invention makes it possible to decorticate the cervical fasciae from the uterine tissue within the cervix.

For this purpose the cervix diameter must be very accurately determined to the millimetre beforehand by transvaginal ultrasonics. A guide rod is then inserted in the uterus, which longitudinally orients the latter and pierces the uterine base as centrally as possible. The basic body of the cervical punch is then engaged on the guide rod and inserted, accompanied by a rotary movement, into the cervical canal, in order to cylindrically punch out the latter with a corresponding, predetermined spacing from the cervical fasciae. The remaining hollow cylinder which is subsequently used for drainage purposes, after transabdanimal or pelvisccpic ligature, can be left behind without any risk with regards to subsequent malignant degeneration. Thus, the patient loses none of her vaginal functions and there is no transvaginal abdominal infection risk. After drawing out the basic body together with the punched out tissue, it is possible to seal open vessels by inserting a cylindrical coagulation probe, namely a hemostat.

The thin-walled, hollow cylindrical, distal part of the basic body has a distal opening, which is provided with a cutting edge. The latter has a very sharp wave grinding pattern which, in the case of a rotary movement of the basic body, brings about an exact cutting in the uterine tissue without the remaining tissue being excessively traumatized. Thus, uterine tissue can be decorticated without deforming the cervical fasciae during this process. At the distal end of the cervical punch on the inside of the hollow cylindrical basic body sharp-edged folding members can be formed which, on retracting the basic body in the proximal direction, swing from the axial position into a radial position and thereby bring about a separation of the punched out uterine tissue at the distal end of the punched out tissue plug.

At its proximal end the basic body has a radially extending, circular handle or grip plate, whose edge is profiled, in order to permit easier operation, particularly with regards to the adjustment of a rotary movement during the cutting process.

The distal half of the length of the basic body is preferably constructed as a thin-walled hollow cylinder for receiving the uterine tissue to be decorticated, whereas the proximal half of the length of the basic body has a through-bore with an internal diameter which only slightly exceeds the external diameter of the guide rod, i.e. is designed with an accurate fit, so that in said proximal area the guide rod is only guided for an axial movement.

The internal diameter transition from the proximal to the distal part is as progressive or conical as possible, to prevent a sticking of removed tissue on corners or edges.

However, it is also possible to make the entire basic body with a thin-walled construction and to provide centering rings in the proximal part, which ensure a central orientation of the guide rod in said body.

The guide rod preferably has an axial longitudinal groove, which ends at a given distance, preferably 6 to 60 nm before the tip, so that no air escapes out of the pneumoperitoneum during the piercing of the base of the uterus. The longitudinal groove is intended to ensure an escape of air from the cervical region and therefore prevents any impediment of the decortication process or a traumatization of the cervical fasciae during decortication.

The entire cervical punch with guide rod is made from V2A steel and can therefore be thermally and chemically sterilized.

The basic body of the cervical punch can be made with different diameters, e.g. 10 to 30 mm. It has a length of preferably 30 cm, while the guide rod can be made much longer than the basic body, e.g. 60 cm. Following the decortication of tissue, the guide rod can also be used for the centered engagement of a hollow cylindrical coagulation probe, in order to permit a hemostasis of remaining uterine tissue within the cervical fasciae.

The basic body provided at the front edge of its distal opening with a wave grinding pattern and which can also be referred to as a morcellator, is advantageously provided with a continuous wave grinding pattern. In this configuration the impression of said pattern in a plane reveals several circumferentially uniformly distributed arcuate portions, which are very clearly spaced from one another. Thus, arc segments of 40° to 45° would e.g. occur in the case of four wave crests and four intermediate wave valleys slightly axially returned into the circumferential surface. The grinding zone of the wave grinding pattern can be present over the entire circumference of the distal opening. However, appropriately said grinding zone is made particularly sharp in the transition area between the crest and the valley of the wave, so that initially there is an axial fixing of the tissue and only subsequently, through the rotary movement of the basic body, a morcellation of tissue cylinders or sleeves. However, the wave grinding pattern can also be discontinuous in the manner of a scale-like arrangement around the circumferential surface at the distal opening.

Although the basic body can be constructed in one piece or non-detachably interconnected with the proximal-side round grip or round gripping ring, further improvements are obtained with a replaceable basic body in said gripping ring. Thus, said replaceability or interchangeability makes it possible to equip an instrrment set of the cervical punch, e.g. with several basic body or morcellator tubes. If the morcellator cutting area wave grinding pattern in particular provided on the outer circumference becanes worn it is easily possible in rapid manner to insert a new morcellator tube. It is also possible as a result of this to have steps in the inside and outside diameter of the basic body or morcellator tube.

The replaceable morcellator tube can be fixed in simple manner by a retaining ring insertable in the inner area of the round gripping ring. Such a retaining ring can be slotted on one side and for material stress reasons has on the opposite side a roughly axially parallel groove in the outer circumference, so that said retaining ring secures by means of diametrically engaging hollow or jaw screws the proximal area of the basic body inserted with press fit. In the proximal direction both the retaining ring and the basic body tube engage against a ring collar having the inside diameter of the basic body tube.

As an alternative to the manual actuation for the rotary movement of the basic body during the punching out or decortication of tissue, it is also possible by means of an electrically, pneumatically or hydraulically driven motor to apply the rotary movement to the basic body. The motor driving shaft can be engaged by means of a toothed ring fitted in non-rotary manner with respect to the outer circumference of the basic body tube and the motor can be fixed to the latter by small ring bearings on either side of the toothed ring.

The invention is described in greater detail hereinafter relative to the drawings, which show:

FIG. 1 a longitudinal section through a rotationally symmetrical basic body of a cervical punch with a distal cutting edge.

Figure 2:
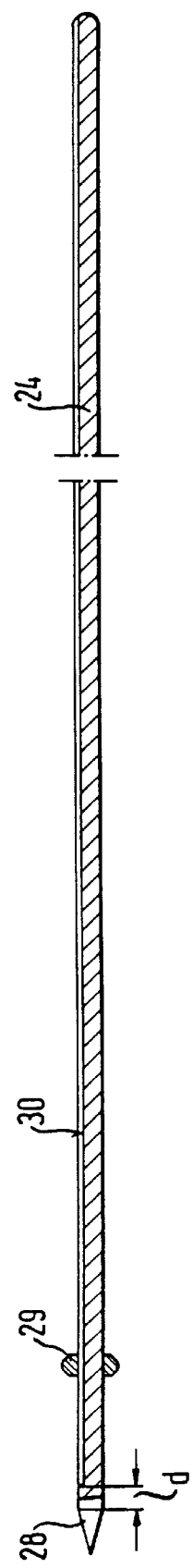

FIG. 2 a longitudinal section through a guide rod.

Figure 3:
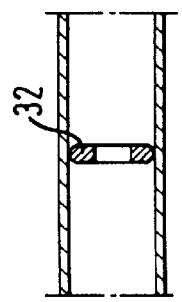

FIG. 3 a larger-scale part of a longitudinal section of a basic body in a further embodiment.

Figure 4:
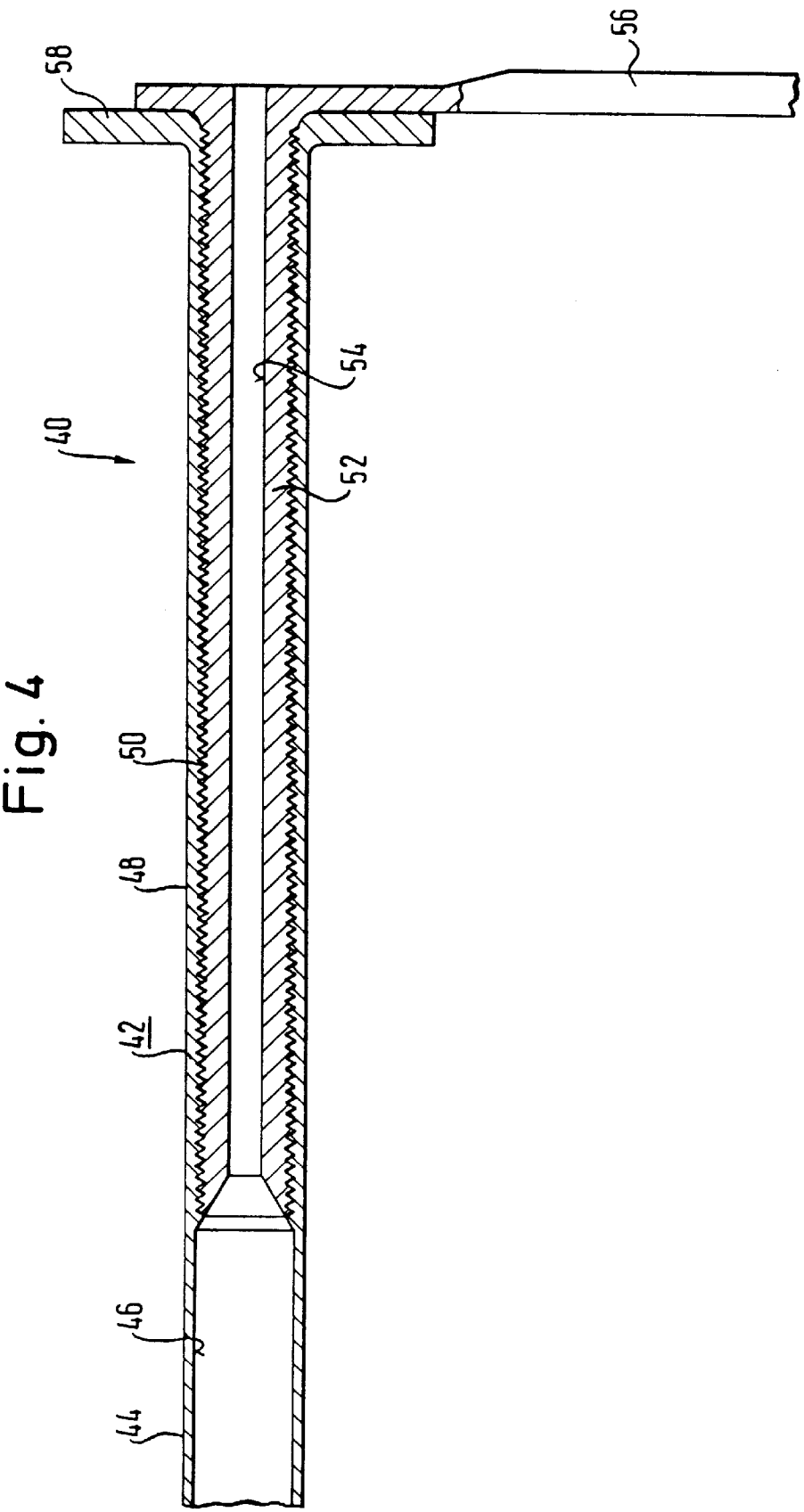

FIG. 4 a longitudinal section through the proximal part of a basic body with a screw insert.

Figure 5:
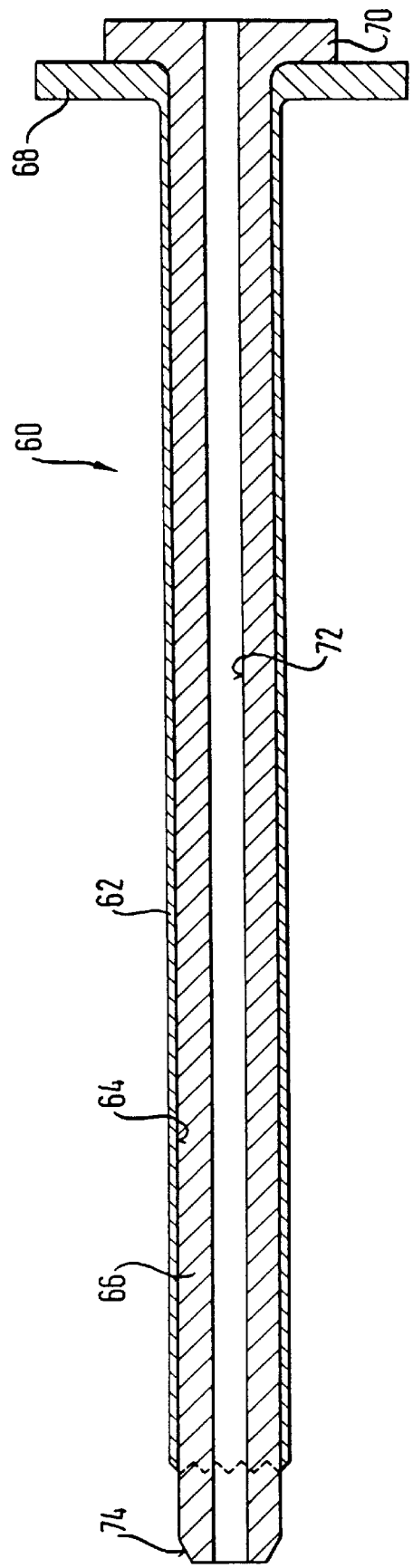

FIG. 5 a longitudinal section through a cervical punch with the basic body and guide cylinder.

Figure 6:
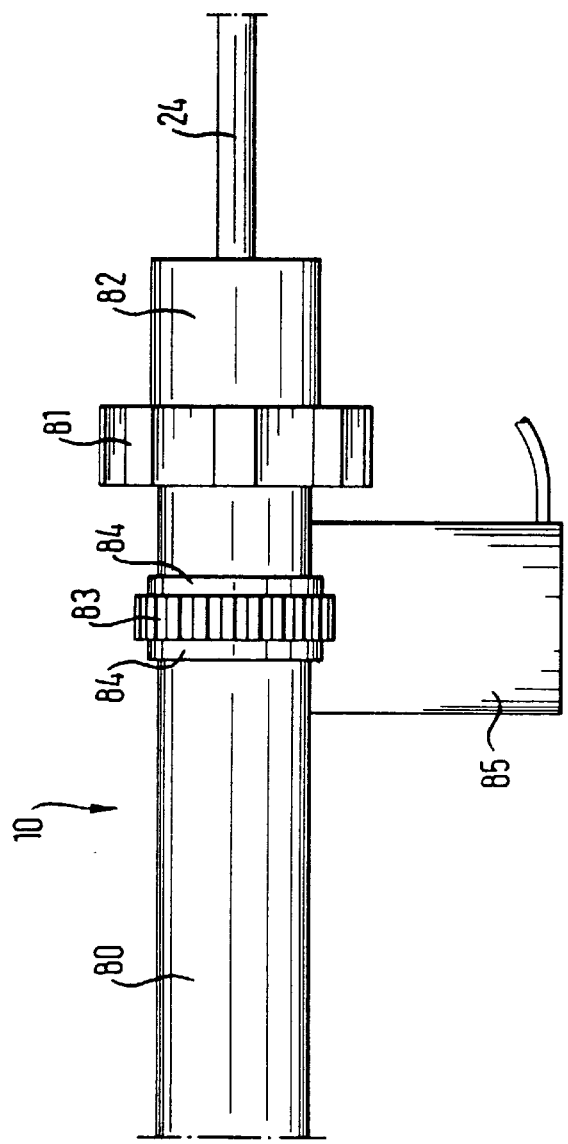

FIG. 6 a diagrammatic representation of another embodiment of the cervical punch with an inner guide cylinder, the rotary movement of the basic body being brought about by means of a motor.

Figure 7:
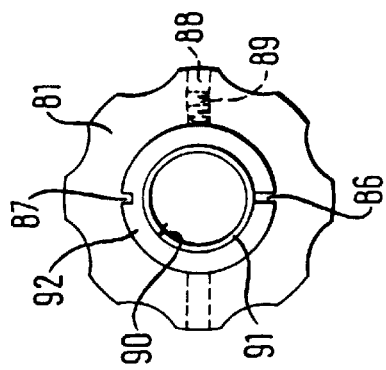

FIG. 7 a diagrammatic plan view of a round gripping ring fittable on the proximal side to the basic body and having an inner retaining ring.

FIG. 1 shows a cervical punch 10 with a hollow cylindrical, rotationally s etrical basic body 12. Over its length the basic body 12 is subdivided into two areas 14, 16, which in each case have a different wall thickness. The distal half 14 of the basic body 12 is constructed as a thin-walled hollow cylinder, whose distal opening 18 has a cutting area 20, which is provided with a rotary wave grinding pattern in the manner of a cutting rim or crown, which can e.g. have roughly twelve cutting waves or corrugations. The proximal part 16 of the hollow cylindrical basic body 12 has a central through-bore 22 with a much smaller diameter than the distal half 14. The inside diameter of the through bore 22 substantially corresponds to the outside diameter of the guide rod shown in FIG. 2, plus a small clearance, in order to ensure a clamping-free, axial displacement of the guide rod 24 in the bore 22. The proximal end of the proximal part 16 of the basic body 12 carries a gripping area 26, which is constructed as a radially directed, circular gripping plate. The gripping plate is connected in non-rotary manner to the basic body 12 and has a profiled edge, e.g. corrugations, in order, through the operation of the gripping plate 26, to rotate the basic body 12, even if handling is difficult and therefore the gripping action reduced.

The distal end of the guide rod 24 is constructed as a conical tip 28. At a distance d of e.g. 6 to 60 mm from said tip 28 an axial longitudinal groove 30 is formed in the guide rod 24. This groove 30 permits a gas exchange between the cervix and the ambient air, so as to prevent an overpressure on introducing the cervical punch into the uterus.

To the guide rod 24 can be fitted a guide ring 29, which is made conical towards its outer circumferential surface. The external diameter of the guide ring 29 is adapted to the internal diameter of the hollow cylindrical basic body 12 of the cervical punch 10 and is used for centering the basic body, which in the embodiment according to FIG. 1 is only guided on the rod 24 in its proximal region 16. Thus, said guide ring 29 brings about a coaxial orientation of the basic body 12 relative to the guide rod 24.

After inserting the guide rod 24 in the uterus and prior to the engagement of the cervical punch 14, it is also possible to fit in adhesive manner a guide ring in the manner of a disk to the mouth of the uterus. By means of the same the cutting rim of the cervical punch is precisely guided, because otherwise in the initial phase of the punching out of the cylindrical tissue on the uterus, it would be possible for there to be a divergence between the guide rod and the cervical punch in the front hollow region.

FIG. 3 shows a partial detail of a longitudinal section on a larger scale compared with FIGS. 1 and 2 through a cervical punch according to FIG. 1 or in some other embodiment.

While the guidance of the guide rod 24 in the cervical punch 10 is mainly ensured by the internal bore 22 of the basic body 12 adapted to the external diameter of the guide rod 24, a guidance of the latter in the basic body of a cervical punch is also made possible by one or more guide rings 32, which are either arranged in axially displaceable manner or are fixed between the basic body and the guide rod.

In the case of the cervical punch 10 of FIG. 1 it is possible to use centering rings 32 in the distal part 14 of the basic body 12. This centering ring 32 moves on punching out the uterine tissue in the direction of the proximal end of the distal part 14.

The transition between the different internal diameters of the distal part 14 and the proximal part 16 of the basic body 12 is preferably progressive, e.g. conical, in order to facilitate cleaning of the instrument and prevent adhesion of tissue to corners and edges.

In an operation for carrying out uterine tissue firstly the guide rod 24 is inserted in the uterus, the latter being oriented, i.e. stretched coaxially to the rod 24 e.g. by further endoscopic instruments. The base of the uterus is then centrally perforated by the tip 28 of the guide rod 24. It is ensured that the tip 28 does not pierce the base of the uterus further than the length d, so that via the groove 30 in the guide rod 24 no gas escapes from the pneumoperitoneum of the abdominal region into the surrounding area. As the guide rod 24 roughly has a length of 60 cm, it projects a long way out of the vaginal region. Onto this projecting part of the guide rod 24 is engaged the basic body 12 of the cervical punch 10 with the distal end at the front. The guide rod 24 passes into the inner guide bore 22 of the proximal part 16 of the basic body 12, so that the latter is centred on the guide rod 12.

By means of ultrasonics, radiology or optical processes the cervix diameter can be established beforehand, so that the external diameter of the basic body 12 can be accurately fixed. The basic body 12, preferably with a permanent rotary movement is turned or shoved in punching manner into the uterus, so that uterine tissue upstream of the distal opening 18 is separated or punched out by means of the cutting edge 20. The separated tissue then passes into the area between the distal part 14 of the basic body 12 and the guide rod 24.

When the distal opening 18 has reached the base of the uterus, the cervical punch is retracted by means of the gripping part, ensuring that the separated tissue located in the distal part 14 of the basic body 12 is also removed from the uterus. For this purpose it is possible to position behind the distal opening 18 flaps with sharp edges, which can be swung from an axial position into a radial position. On retracting the cervical punch 12 said parts are swung into a radial position and therefore separate the uterine tissue in the distal part 14 from the remaining uterine tissue in the vicinity of the distal opening 18.

After drawing out the cervical punch a hollow cylindrical coagulation probe or hemostat can be engaged over the remaining guide rod 24. This hemostat makes it possible to close open vessels of the remaining uterine tissue by heat treatment and bring about a hemostasis.

FIG. 4 shows a cervical punch 40 with a basic body 42, which over its entire length is constructed as a thin-walled hollow cylinder. In its distal part 44 the inner wall 46 of the basic body 42 is made smooth for receiving tissue to be punched out. The proximal part, particularly the proximal half 48 of the basic body 42, has on the inner wall of the hollow cylinder a screw thread 50, which engages in a complimentary external thread on the outer circumference of a screw insert 52 constructed as a guide cylinder and which has a bore 54 for the guide rod 24. The screw insert 52 projects at its proximal end out of the proximal part 48 of the basic body 42. At this point the screw insert 52 has a radially extending gripping part 56, which is used for holding the screw insert 52 in rotation-preventing manner, while the proximal gripping plate 58 of the basic body 42 is screwed into the uterus. The screw insert 52 in the axial direction remains firmly connected to the guide rod, for example, a force fit connection or a locking connection. The guide rod is fixed in the base of the uterus. Through the securing of the screw insert 52 and the rotary movement of the basic body 42 relative to the screw insert 52, a clearly defined axial movement is superimposed on a rotary movement, which assists the cutting edge at the distal end of the cervical punch 40 in its corresponding cutting action.

It is obviously possible to select the length of the screw insert 52 in such a way that it extends over the entire length of the basic body 42, or to have it project distally out of said body 42. The internal thread 50 could be arranged over the entire length in the basic body 42. However, preferably a distal area of the basic body is kept thread-free. If the screw insert 52 and the basic body 42 only have a complementary thread in the proximal part, the external diameter of the screw insert 52 serving as the guide cylinder must be reduced on the root of the screw thread, so that the part of the basic body provided with the internal thread can be engaged over the thread-free part of the screw insert. Preferably, the basic body and the screw insert or the guide cylinder have a length of 250 mm and the external diameter of the basic body is preferably 10, 15 or 20 mm.

The pitch of the thread 50 can be approximately 8 mm. Through the rotational speed of the hollow cylindrical basic body 42 about the guide cylinder, it is consequently possible to thread-control the advance speed of the basic body and therefore the cutting speed of the distal cutting rim 20 on the basic body and this can be relatively accurately maintained by assisting personnel.

The radial gripping part 56 can also be constructed as a fastening for a not shown bullet forceps with which the vaginal region can be clamped during the operation.

FIG. 5 shows a cervical punch 60 comprising a thin-walled, hollow cylindrical basic body 62, whose inner wall 64 is made smooth for receiving a hollow cylindrical guide cylinder 66. At its proximal end the basic body 62 has a radial gripping plate 68 for the operation of the instrument. The proximal end of the guide cylinder 66 is also radially widened in the manner of a gripping plate 70. In the completely inserted state the gripping plate 70 of the guide cylinder 66 engages on the gripping plate 68 of the basic body 62. The guide cylinder 66 has an axial through-bore 72 as a guide for receiving a guide rod 24.

In the fully inserted state according to FIG. 5 the distal end 74 of the guide cylinder 66 projects over and beyond the basic body 62 and consequently permits a centering thereof in the vicinity of the mouth of the uterus, particularly at the start of the operation.

The edges between the front face and the circumferential surface at the distal end of the guide cylinder 66 are preferably made conical for better guiding the cervical punch 60.

FIG. 6 shows in fragmentary manner the proximal region of a cervical punch 10 with a motor drive. The basic body. or the morcellator tube 80 is provided at the proximal side with a round gripping ring 81, which is located on a round gripping ring 82, which is e.g. rigidly connected to a guide cylinder provided in the morcellator tube 80. Both round gripping rings 81, 82 are provided with marginal depressions, so as to permit better manual actuation. The proximal projecting guide rod 24 extends through the guide cylinder with the round gripping ring 82.

For improving comfort during the operation of the cervical punch and ensure a precise, reliable cutting or punching process a motor 85 is shown in FIG. 6. This electrically operated motor 85 engages e.g. by means of a worm thread in a toothed rim 83 fitted in non-rotary manner to the outer casing of the morcellator tube 80. On either side of said toothed ring are fitted ball races 84, to which the motor 85 is fixed. It is possible in this way, e.g. with a rotary movement of e.g. 60 to 80 r.p.m., to rapidly and very accurately perform a decortication process with respect to the cervix.

FIG. 7 shows in axial plan view towards the proximal end the round gripping ring 81 without the morcellator tube 80. In the inner opening of the round gripping ring 81 is placed in relatively accurately fitting manner a retaining ring 92, which terminates in surface-flush manner with the round gripping ring 81 and at the proximal side engages against a ring collar 91 against which also strikes the proximal end of the morcellator tube 80. The retaining ring 92 is slotted at 86 and has a groove 87 on its outer circumference diametrically facing the same. Both measures permit a slight inwardly directed tightening of the retaining ring, so that the morcellator tube 80 can be received with force fit in both rotary and axially fixed manner. For this adjustment possibility is provided displaced 90° from the slot 86 a bore 88 in the round gripping ring 81 and permits by means of a hollow screw 89 and corresponding screw thread a pretensioning of the retaining ring 92 in the radial inwards direction. As the internal diameter 90 of the retaining ring already has press fit with the outer circumference of the morcellator tube 80, this permits a reliable, simple fixing and also a replacement of the morcellator tube 80.

I claim:

1. A cervical punch comprising:
   a hollow cylindrical basic body having an opening at its distal end with a cutting region and an engagement region at its proximal end; and
   guiding means for guiding said basic body, said basic body being movable relative to the guiding means;
   said engagement region providing for rotation of said basic body relative to said guiding means;
   wherein said basic body is a circular tube with an outside diameter remaining substantially constant between said engagement region and said opening and said cutting region is a portion of said circular tube and is formed as a wave grinding pattern extending all around said opening, said wave grinding pattern including segments of a circle distributed over its circumference with axially set back wave valleys and with axially protecting wave crests, wherein said guiding means comprises a guide rod receivable within said basic body, and a hollow cylindrical guiding means for centrally receiving said guide rod is defined by said circular tube, and wherein said guide rod includes an axially running longitudinal groove which is separated from a tip of said guide rod by a given distance.

2. A cervical punch comprising:

a hollow cylindrical basic body having an opening at its distal end with a cutting region and an engagement region at its proximal end; and guiding means for guiding said basic body, said basic body being movable relative to the guiding means;

said engagement region providing for rotation of said basic body relative to said guiding means;

wherein said basic body is a circular tube with an outside diameter remaining substantially constant between said engagement region and said opening and said cutting region is a portion of said circular tube and is formed as a wave grinding pattern extending all around said opening, wherein said circular tube includes a distal portion and a proximal portion with different internal diameters and wherein a transition between the diameters is continuous.

3. A cervical punch comprising:

a hollow cylindrical basic body having an opening at its distal end, a cutting region defined at said distal end and an engagement region at its proximal end;

a guide rod for guiding said basic body, said engagement region providing for rotation of said basic body relative to said guide rod;

said basic body being a circular tube with an outside diameter which remains substantially constant along its total length, said cutting region defined at said distal end of said basic body and providing a wave grinding pattern extending all around said opening; and a screw insert, forming a guide cylinder, held in a rotatable and axially movable manner in said circular tube by a screw thread, said screw insert including a bore for centrally receiving said guide rod.

4. A cervical punch according to claim 3, characterized in that said screw insert is adapted to be fixed on said guide rod by a force fit connection.

5. A cervical punch according to claim 3, characterized in that said screw insert includes a portion, projecting out of the proximal end of said basic body, having a radially extending gripping portion.

* * * * *